United States Patent

Johnson

[11] Patent Number: 5,899,907
[45] Date of Patent: May 4, 1999

[54] INSTRUMENTATION FOR PROXIMAL FEMORAL COMPACTION BROACHING

[76] Inventor: Lanny L. Johnson, 4528 Hagadorn, East Lansing, Mich. 48823

[21] Appl. No.: 08/734,383

[22] Filed: Oct. 17, 1996

Related U.S. Application Data

[63] Continuation of application No. 08/309,592, Sep. 21, 1994, abandoned, which is a continuation-in-part of application No. 08/111,970, Aug. 26, 1993, abandoned, which is a continuation of application No. 07/848,546, Mar. 9, 1992, abandoned, which is a division of application No. 07/721,893, Jun. 27, 1991, Pat. No. 5,116,337.

[51] Int. Cl.$^6$ ..................................................... A61B 17/56
[52] U.S. Cl. .............................................. 606/73; 606/86
[58] Field of Search ................................ 606/79, 80, 81, 606/83, 84, 85, 86

[56] References Cited

U.S. PATENT DOCUMENTS

| | | | |
|---|---|---|---|
| 1,384,330 | 7/1921 | Moshier | 606/84 X |
| 2,514,665 | 7/1950 | Myller | 606/80 X |
| 4,302,855 | 12/1981 | Swanson | 606/95 |
| 4,474,177 | 10/1984 | Whiteside | 606/80 |
| 4,524,766 | 6/1985 | Petersen | 606/85 |
| 4,657,002 | 4/1987 | Ray | 606/79 |
| 4,697,584 | 10/1987 | Haynes | 606/95 |
| 5,057,112 | 10/1991 | Sherman et al. | |
| 5,089,004 | 2/1992 | Averill et al. | 606/85 |
| 5,100,407 | 3/1992 | Conrad et al. | 606/79 |
| 5,437,675 | 8/1995 | Wilson | 606/80 |

FOREIGN PATENT DOCUMENTS

| | | |
|---|---|---|
| 3630069 C1 | 9/1986 | Germany . |
| WO 93/01773 | 2/1993 | WIPO . |

*Primary Examiner*—Michael Buiz
*Assistant Examiner*—Daphna Shai
*Attorney, Agent, or Firm*—Pillsbury Madison & Sutro LLP

[57] ABSTRACT

Instrumentation for preparing a femur for implantation of a prothesis therein, the femur including a femoral shaft having a femoral canal therein defined by sidewalls, the prosthesis being constructed and arranged to be received within the femoral canal, the instrumentation including: at least one initial compactor instrument having a proximal portion and a distal broach portion, the broach portion being adapted to conform substantially to a proximal end of the femoral canal so as to compact bone in the sidewalls thereof without intentionally removing bone from the femoral canal; a second type of compactor instrument having a proximal portion and a distal broach portion, the secondary compactor instrument portion being constructed and arranged to conform substantially to the shape of the prosthesis so as to further compact bone in the sidewalls of the proximal end of the femoral canal such that the compacted sidewalls conform substantially to the shape of the prosthesis; and a final type of compactor instrument having a proximal portion and an elongated distal broach portion, the elongated broach portion being adapted to extend into the femoral canal and compact bone in sidewalls of the femoral canal at a location distal to previously compacted sidewalls of the proximal end of the femoral canal.

10 Claims, 3 Drawing Sheets

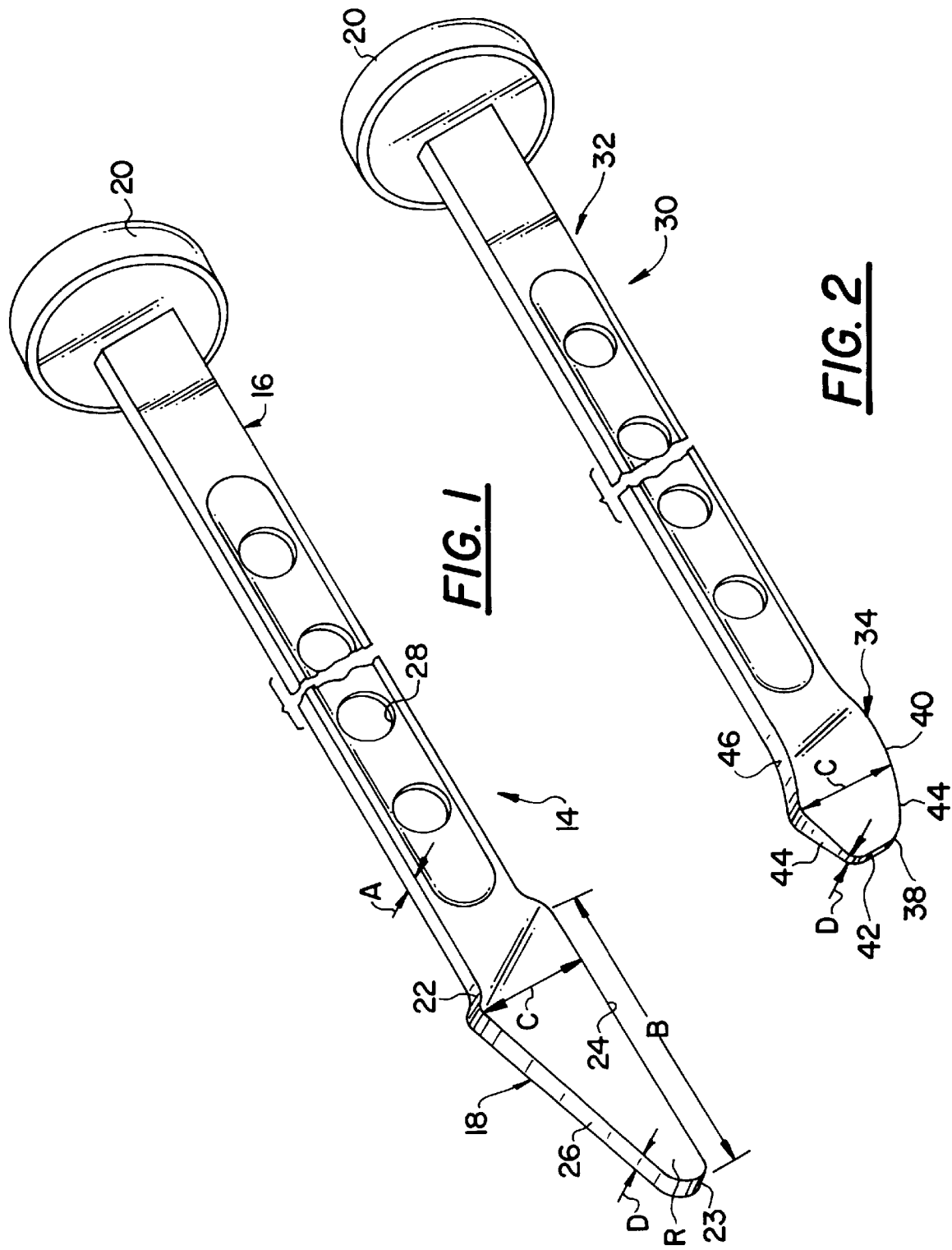

INSTRUMENTATION FOR PROXIMAL FEMORAL COMPACTION BROACHING

This is a continuation of Application No. 08/309,592, filed on Sep. 21, 1994, now abandoned, which was a continuation-in-part of Application No. 08/111,970, filed on Aug. 26, 1993, now abandoned, which was a continuation of Application No. 07/848,546, filed on Mar. 9, 1992, now abandoned, which was a division of Application No. 07/721,893, filed on Jun. 27, 1991, now U.S. Pat. No. 5,116,337.

BACKGROUND OF THE INVENTION

The present invention relates to implanting prosthesis devices, and, more particularly, to the preparation of the femur for implanting a prosthetic hip replacement device therein.

Bone disease and injuries to joints often make it necessary or desirable to replace a natural joint with an artificial prosthesis. One such replacement involves the fixation of a prosthetic hip joint to a proximal end of the femur. The femur contains a hollow intramedullary femoral canal running through a central axis thereof. When implanting the joint prosthesis into the femur, it is desirable to fix the prothesis to the femur in such a manner that the stem of the prosthesis lies along the central axis of the femur. In preparing the proximal end of the femur to receive the prosthesis, the femoral head is first removed, exposing the femoral canal. If the femoral canal is large enough to accommodate the prosthesis, the prosthesis is then inserted into the canal and fixed to the femur either by an interference fit or by cement fixation. In certain circumstances, the femoral canal is not wide enough to accommodate the prosthesis; thus, the canal is enlarged by drilling or the like to a size appropriate for receiving the stem of the prosthesis at the proximal end of the femur. The femur comprises hard cortical bone surrounding softer porous bone, which lines the femoral canal. Prior to and after drilling to open the femoral canal for insertion of the prosthesis therein, the density of the porous bone remains low at the wall of the femoral canal. Due to the low-density canal wall, fixation of the prosthesis to the femur may deteriorate over time.

SUMMARY OF THE INVENTION

An object of the present invention is to provide a series of instruments for use in preparing a femur for implantation of a prosthesis device. The instruments are sized and configured for sequential dilation of the bone lining the femoral canal. The dilation results in compacting bone, thereby defining high density canal walls which increases the fixation properties between the femur and prosthesis. In accordance with the principles of the present invention, this objective is obtained by providing a kit of instruments for preparing a femur for implantation of a prothesis therein, the femur including a femoral shaft having an exposed femoral canal therein defined by sidewalls, the prosthesis being constructed and arranged to be received within the femoral canal. The kit includes at least one initial type of compactor instrument having a proximal portion and a distal broach portion, the broach portion being constructed and arranged to conform substantially to a proximal end of the femoral canal so as to compact bone in the sidewalls thereof without intentionally removing bone from the femoral canal. A second type of compactor instrument is provided which also has a proximal portion and a distal broach portion, the latter being constructed and arranged to conform substantially to a shape of the prosthesis so as to further compact bone in the sidewalls of the proximal end of the femoral canal so that they conform substantially to the shape of the prosthesis. A third type of compactor instrument is provided and has a proximal portion and an elongated distal broach portion. The elongated broach portion is constructed and arranged to extend into the femoral canal and compact bone in sidewalls of the femoral canal at a location distal to previously compacted sidewalls of the proximal end of the femoral canal.

In accordance with a further aspect of the invention, a method is provided for preparing internal walls of a cavity in bone for receiving a medical device within the cavity. The method includes the steps of selecting a sizing instrument capable of compacting which comprises the internal wall of the cavity; compacting the bone which comprises the internal wall, without intentionally removing bone from the cavity, by inserting the selected sizing instrument within the cavity; and continuing compacting the bone until the sidewalls of the cavity include dense, compacted bone resisting migration or translocation of a medical device placed therein.

Other objects, features and characteristics of the present invention, as well as the function of the related elements of the structure, and the economics of manufacture, will become more apparent upon consideration of the following detailed description and appended claims with reference to the accompanying drawings, all of which form a part of the specification.

BRIEF DESCRIPTION OF THE DRAWINGS

FIG. 1 is a perspective view of an initial femoral compactor instrument for use in compacting bone in the femur, provided in accordance with the principles of the present invention;

FIG. 2 is a perspective view of a second type of femoral compactor instrument constructed and arranged to conform to the configuration of a prothesis to be inserted into the femur;

DETAILED DESCRIPTION OF THE PRESENTLY PREFERRED EXEMPLARY EMBODIMENT

Figure 3:
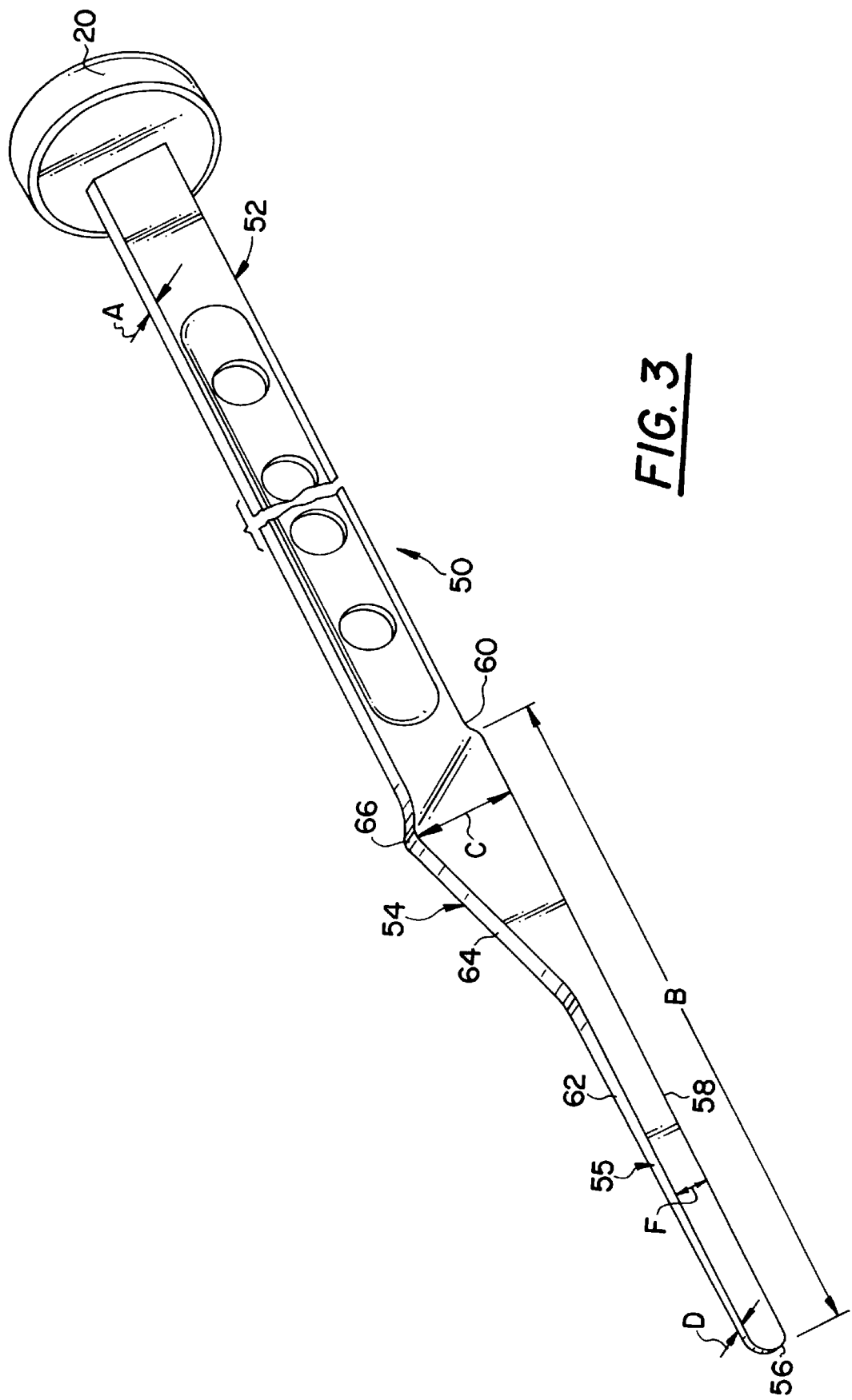
FIG. 3 is a perspective view of a third or final type of femoral compactor instrument for compacting bone deep within the femoral shaft.

FIGS. 1–3 show a series of femoral compaction instruments defining a kit for use in preparing a femoral cavity or canal 10 (FIGS. 4–6) of a femur 12 for insertion of a femoral prosthesis device (not shown) into the canal 10.

FIG. 1 illustrates an initial femoral compactor instrument, generally indicated at 14, comprising a proximal portion 16 and a distal broach portion 18. The proximal portion 16 terminates in an enlarged head 20 which is constructed and arranged to be contacted by a hammer or mallet for use in inserting the instrument 14 into the femur, as will be explained below. The proximal portion 16 is of generally rectangular cross-section having a width A of approximately 10 mm. The proximal portion 16 merges with the broach portion 18 via curved segment 22. The broach portion 18 is constructed and arranged to conform substantially to a proximal end of the femoral canal 10. Thus, as shown in FIG. 1, the broach portion 18 is of generally triangular configuration having a blunt, rounded tip 23. The radius R of the tip 23 is approximately 5 mm. The broach portion 18 has a planar base segment 24, approximately 70 mm in length, as shown by dimension B. The base segment 24 merges smoothly with the rounded tip 23 at one end thereof and merges smoothly with segment 22 at the other end thereof. The broach portion 18 also includes an upper segment 26 which extends from the tip 23 towards the curved segment 22 at an acute angle with respect to the base segment 24. The maximum height C of the broach portion 18 is approximately 25 mm, and the width D is in the range of 2–4 mm. It is within the contemplation of the invention to include a plurality of initial instruments 14 with the kit, each instrument 14 having slightly increasing broach portion widths. For example, one instrument 14 may have a broach portion width D of 2 mm, another, 3 mm and yet another, 4 mm. The instrument 14 is used to compact bone in the femoral canal 10, and the availability of a series of increasing widths for the broach portion 18 assists in achieving the desired dilation of the femoral canal 10, as will be explained more fully below.

The broach portion 18 is formed integrally with the proximal portion 16, preferably from stainless steel or like material suitable for medical purposes. As shown in FIG. 1, the broach portion 18 is solid, while in the illustrated embodiment, the proximal portion 16 includes a plurality of spaced bores 28 therethrough which reduces the amount of material required to manufacture the instrument 14, without diminishing its strength. Of course, the proximal portion 16 may be formed as a solid member, if desired.

FIG. 2 shows a second type of femoral compactor instrument, generally indicated at 30, including a proximal portion 32 and a distal broach portion 34. The proximal portion 32 is identical to the proximal portion 16 of the initial instrument 14 of FIG. 1. Thus, the description of the proximal portion 32 need not be repeated here. The broach portion 34 is a solid member constructed and arranged to conform generally to the configuration of the prothesis to be implanted into the femoral canal 10. In the illustrated embodiment, broach portion 34 is generally short and blunt, as compared to the corresponding portion of instrument 14 of FIG. 1, so as to permit bone in a different portion of the femoral canal 10 to be compacted. The broach portion 34 has a maximum height C of approximately 25 mm and a width D which tapers from approximately 10 mm at the juncture between the proximal portion 32 and the broach portion 34 to approximately 5 mm at the tip 38 of the broach portion 34. Portion 34 includes a curved segment 40, an end segment 42, two tapered segments 44, each extending from the end segment 42, and an upper curved segment 46 merging with the proximal portion 32. These peripheral segments of the broach portion 34 are constructed and arranged to compact bone in the femoral canal 10. It is contemplated by the invention to use instrument 30, after instrument 14 has been employed, to further compact bone in preparing the femur for receiving the prosthesis, as will become apparent below. Further, it is contemplated to include a plurality of these second type of instruments 30 with the kit, each such instrument 30 having slightly increasing broach portion widths.

FIG. 3 shows a third, or final type of femoral compactor instrument contained in the kit. The third femoral compactor, generally indicated at 50, is used preferably after compaction has been performed with the second type of instrument 30. As with the instrument of FIG. 2, the proximal portion 52 of instrument 50 is identical to the proximal portion 16 of the instrument of FIG. 1. As shown in FIG. 3, the distal broach portion 54 of instrument 50 is similar to the broach portion 18 of instrument 14, but further includes an elongation, generally indicated at 55, to the distal broach portion 54. The broach portion 54 of instrument 50 has an overall length B of approximately 160 mm and a maximum height C of approximately 25 mm. The elongation 55 has a length of approximately 90 mm, a height F of approximately 9 mm, and a width D which tapers from approximately 10 mm at one end thereof to approximately 5 mm at the distal end 56 of the broach portion 54.

As shown in FIG. 3, the instrument 50 includes a planar base segment 58 spanning the length of the broach portion 54. The base segment 58 merges smoothly with the rounded tip 56 and also mezges smoothly with the proximal portion 52 at end 60 thereof. The broach portion 54 also includes an upper segment 62 which extends generally parallel to the base segment 58 from the tip 56 towards the proximal portion 52, a distance of approximately 90 mm. A top segment 64 extends at an acute angle from the upper segment 62 and merges with the proximal portion 52 at end 66. These peripheral segments are constructed and arranged to compact bone deep within the femoral canal 10. The broach portion 54 is solid and made of stainless steel or similar materials. As with the other types of instruments in the complete kit, it is contemplated to include a plurality of the third or final type, such instruments 50 having slightly increasing broach portion widths.

Figure 4:
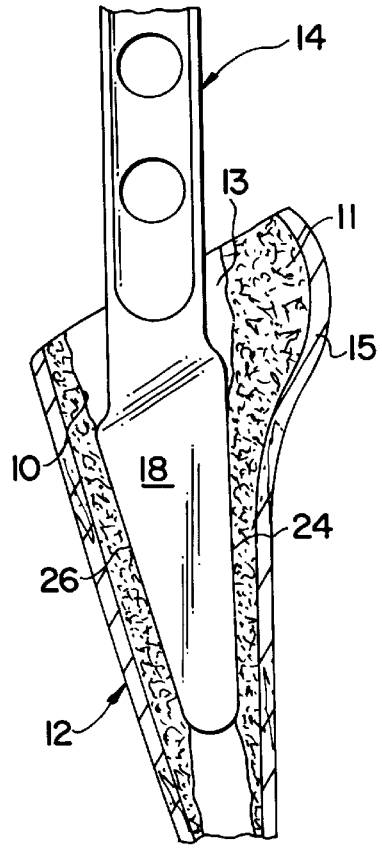
FIG. 4 is a partial schematic view of the compactor instrument of FIG. 1, shown inserted into the femoral canal and compacting bone at a proximal end of the femur.
Figure 5:
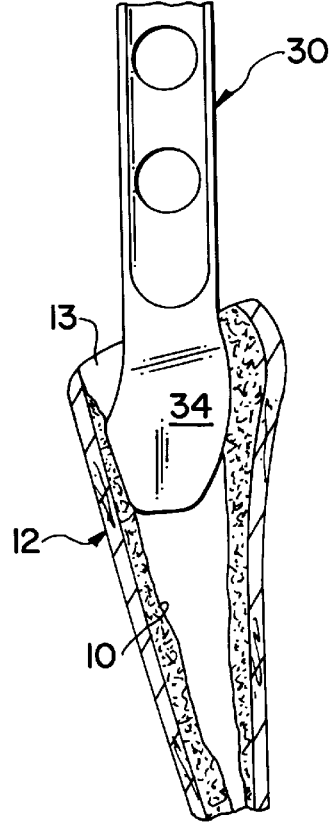
FIG. 5 is a view of the compactor instrument of FIG. 2, shown in position to further compact bone at the proximal end of the femur.
Figure 6:
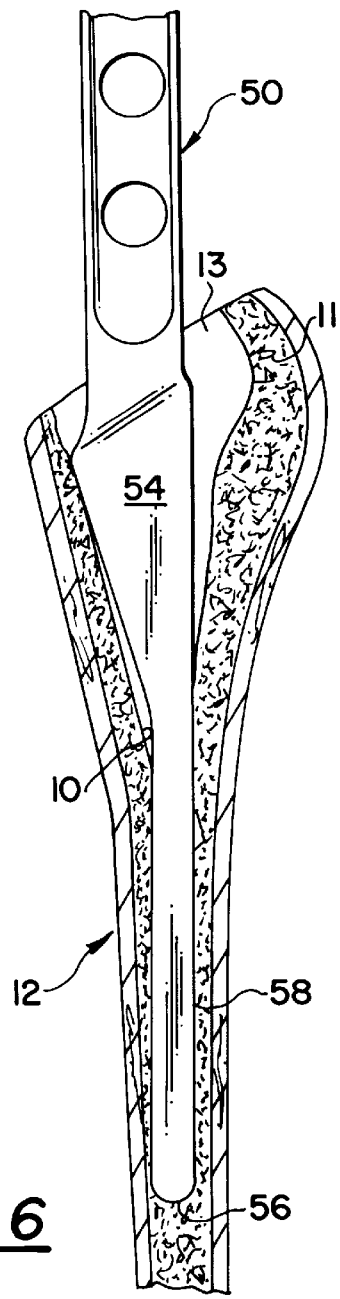
FIG. 6 is a view of the compactor instrument of FIG. 3, shown in position to compact bone within the femoral shaft.

With reference to FIGS. 4–6, the use of the instruments of the kit to prepare a femur for receiving a prosthesis will be described. The first step in a procedure for preparing the femur is to expose the proximal femoral neck and shaft of the femur by removing the femoral head (not shown). The orientation and direction of the femoral canal 10 is then determined for proper instrument placement. If the canal width is narrow, or a cortical fit is desired, the surgeon first drills the canal 10 in a reverse drill operating mode to prevent removal of bone from the canal 10. If such a drilling operation is not possible, then a forward aggressive drilling mode is used, alternated with reverse drilling, so as to preserve bone fragments within the canal for compaction along the anticipated prosthesis route. If the canal width is larger than the prothesis to be used, then no drilling is required, and the instruments comprising the invention are sufficient to prepare the femur for the prothesis placement.

When the instruments contained in the kit are utilized to compact bone to prepare the femur for the prosthesis implant, a 2 mm wide initial femoral compactor 14 first is grasped at the proximal portion 16 thereof and is pushed and/or impacted with a mallet on its head 20 to insert the broach portion 18 thereof into the proximal portion 13 of the femoral canal 10, such that the peripheral segments of the broach portion 18, in particular, segments 24 and 26, displace the softer bone 11 in the sidewalls of the canal 10. The instrument 14 is then removed from the canal 10. After compaction with the 2 mm width initial instrument 14, the 3 mm and the 4 mm width instruments 14 may be inserted sequentially into the canal 10 to further compact bone in the sidewalls thereof, if desired.

Next, as shown in FIG. 5, the second type of femoral compactor instrument 30 is inserted into the femoral cavity 10 in a similar manner as the initial compactor instrument(s) 14, and along the same orientation plane. Instrument 30 is also pushed and/or impacted at its head 20 so the peripheral surfaces of broach portion 34, particularly segments 40 and 44, compact bone in the sidewalls of the canal 10 so that the compacted sidewalls correspond to the shape of the prosthesis to be inserted into the canal 10. It is within the contemplation of the invention to customize the geometry of the broach portion 34 of the second type of femoral compactor instrument 30 to correspond to the geometry of the implant under consideration. Additional instruments 30 having slightly increasing broach portion widths can be used sequentially to dilate a portion of the canal 10, if desired.

Next, the final type of femoral compactor instrument 50 is inserted into the canal 10 in the manner described above, along the same orientation plane as the previously employed instruments. The elongated broach portion 54 of instrument 50 creates compaction of the softer bone 11 in the sidewalls deep within the femoral canal at a location distal to the previously compacted proximal portion 13 of the femoral canal 10, as shown in FIG. 6. If desired, additional instruments 50 having slightly increasing widths can be used sequentially to dilate a portion of the canal 10 deep within the femur.

After using the instruments of the kit to compact bone of the femur, the femur is now ready to receive a prosthesis (not shown) therein. The procedure which has been described for preparing the femur may be used when implanting either a cemented or non-cemented prosthesis.

The method described for preparing a femur for insertion of a femoral component for total hip replacement provides an effective means of compacting bone by the use of a series of compaction instruments to produce dense sidewalls of the canal 10 for receiving the prothesis. Such density of the sidewalls of the canal 10 ensures a degree of bone compactness which creates high resistance to migration or translocation of the prothesis inserted into the prepared femur. The dense bone wall of the canal 10 provides resistance to angular or rotational stress of the prosthesis secured to the wall of the canal. Thus, the use of the instrumentation kit of the invention to compact bone clearly offers significant advantages over conventional femoral prosthesis insert preparation, wherein either nothing is done to the canal sidewalls, or wherein the canal is prepared by removing bone via drilling.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A bone compaction instrumentation kit for compacting bone along a sidewall of a canal formed within a femoral shaft of a femur, the instrumentation kit comprising:
    at least one initial compaction instrument having a proximal portion and a distal broach portion, said broach portion having an exterior compacting surface which, when the broach portion is inserted within the canal, compacts bone along the sidewall without intentionally removing bone from the canal;
    at least one second compaction instrument having a proximal portion and a distal broach portion, said broach portion being differently sized and contoured relative to the first compaction instrument and having an exterior compacting surface which, when inserted within the canal, further compacts bone along the sidewall, and
    at least one third compaction instrument having a proximal portion and a distal broach portion, said broach portion being differently sized and contoured relative to the first and second compaction instruments and having an exterior compacting surface which, when inserted into the canal further compacts bone along the sidewall.

2. A bone compaction instrumentation kit according to claim 1, wherein the broach portion of said initial compaction instrument has a length of approximately 70 mm, a maximum height of approximately 25 mm and a width in the range of approximately 2 to 4 mm.

3. A bone compaction instrumentation kit according to claim 1, wherein the broach portion of said second compaction instrument has a maximum height of approximately 25 mm and a width which tapers from approximately 10 mm to approximately 5 mm towards a distal end thereof.

4. A bone compaction instrumentation kit according to claim 1, wherein the broach portion of said third compaction instrument has a maximum height of approximately 25 mm, a width of approximately 10 mm and a length of approximately 70 mm, and wherein the broach portion of said third compaction instrument has an elongated portion with a length of approximately 90 mm, a height of approximately 9 mm and a width which tapers from approximately 10 mm at one end thereof to approximately 5 mm at a distal end thereof.

5. A bone compaction instrumentation kit according to claim 1, wherein said proximal portion of each compaction instrument includes a head formed so as to be impacted to drive the compaction instrument into the femoral canal.

6. A bone compaction instrumentation kit according to claim 1, wherein each compaction instrument is made of stainless steel.

7. A bone compaction instrumentation kit according to claim 1, wherein at least one of said initial compaction instrument, said second compaction instrument and said third compaction instrument comprises a plurality of instruments of different width.

8. A bone compaction instrumentation kit for compacting bone along substantially an entire internal wall of a cavity formed within the bone in preparation for receiving a medical device within the cavity, the instrumentation kit comprising:
    a first compaction instrument having a proximal portion and a distal portion, said distal portion being configured and sized relative to the dimensions of said cavity whereby an exterior compacting surface of the instrument compacts bone along said internal wall when the distal portion of the first instrument is inserted within the cavity; and
    at least two additional compaction instruments each having a proximal and a distal portion, said distal portion of the additional compaction instruments being differently sized and contoured relative to one another, and relative to the first compaction instrument, and having exterior compacting surfaces whereby after compaction of bone on the internal wall of the cavity by said first compaction instrument, insertion of successively larger distal portions of the respective additional compaction instruments into the cavity so as to bring the exterior compacting surfaces of the additional compaction instruments into engagement with said internal wall further compacts bone along said internal wall.

9. A bone compaction instrumentation kit according to claim 8, wherein said proximal portion of each compaction instrument includes a head formed so as to be impacted to drive the respective compaction instrument into the cavity.

10. A bone compaction instrumentation kit according to claim 8 or 9, wherein each compaction instrument is made of stainless steel.

* * * * *